United States Patent
Krause et al.

(10) Patent No.: US 6,207,610 B1
(45) Date of Patent: *Mar. 27, 2001

(54) COMPACTS BASED ON PYROGENICALLY PRODUCED SILICON DIOXIDE

(75) Inventors: Helmfried Krause, Rodenbach; Hermanus Lansink Rotgerink, Glattbach; Thomas Tacke, Friedrichsdorf; Peter Panster, Rodenbach; Roland Burmeister, Geiselbach, all of (DE)

(73) Assignee: Degussa-Huls AG, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/857,491

(22) Filed: May 16, 1997

Related U.S. Application Data

(60) Provisional application No. 60/021,808, filed on Jul. 16, 1996.

(30) Foreign Application Priority Data

May 17, 1996 (DE) .............................. 196 19 961

(51) Int. Cl.$^7$ .............................. B01J 21/08; C04B 35/14; C04B 14/04; C01B 33/112
(52) U.S. Cl. .................. 502/232; 502/243; 502/245; 502/258; 502/261; 502/262; 501/133; 501/154; 423/335; 423/337; 106/481; 106/482
(58) Field of Search .................. 502/170, 243, 502/251, 300, 263, 232, 63, 509, 245, 258, 261, 262; 501/133, 154; 423/335, 337; 106/481, 482

(56) References Cited

U.S. PATENT DOCUMENTS

| | | | |
|---|---|---|---|
| 4,087,622 | * 5/1978 | Nakamura et al. | 502/170 |
| 4,482,642 | 11/1984 | Ettliner et al. | 502/232 |

(List continued on next page.)

FOREIGN PATENT DOCUMENTS

| | | |
|---|---|---|
| 2 168 677 | 8/1996 | (CA) . |
| 3132674 | 3/1983 | (DE) . |

(List continued on next page.)

*Primary Examiner*—Mark L. Bell
*Assistant Examiner*—Patricia L. Hailey
(74) *Attorney, Agent, or Firm*—Pillsbury Madison & Sutro LLP

(57) ABSTRACT

Compacts based on pyrogenically produced silicon dioxide and having the following physical and chemical characteristics:

| | |
|---|---|
| Outer diameter | 0.8–20 mm |
| BET surface area | 30–400 m$^2$/g |
| Pore volume | 0.5–1.3 ml/g |
| Breaking strength | 10–250N |
| Composition | >99.8 wt. % SiO$_2$ |
| Other constituents | <0.2 wt. % |
| Abrasion | <5 wt. % |
| Apparent weight | 350–750 g/l | are produced in that pyrogenically produced silicon dioxide is homogenized with methyl cellulose, microwax and polyethylene glycol with addition of water, dried at a temperature of 80–150° C. and comminuted to a powder, optionally the powder is compressed into compacts, and heat-treated at a temperature of 400 to 1200° C. for a time of 0.5 to 8 hours. These compacts can be used as catalysts or catalyst carriers in vinyl acetate monomer production and ethylene hydration.

7 Claims, 2 Drawing Sheets

U.S. PATENT DOCUMENTS

| | | | |
|---|---|---|---|
| 4,919,843 | * 4/1990 | Innertsberger et al. | 252/358 |
| 5,002,918 | * 3/1991 | Deller et al. | 502/263 |
| 5,021,378 | * 6/1991 | Deller et al. | 502/62 |
| 5,086,031 | 2/1992 | Deller et al. | 502/251 |
| 5,250,487 | 10/1993 | Wirtz et al. | 502/243 |
| 5,332,710 | * 7/1994 | Nicolau et al. | 502/243 |
| 5,610,116 | * 3/1997 | Werdecker et al. | 502/263 |
| 5,776,240 | * 7/1998 | Deller et al. | 106/482 |
| 5,858,906 | * 1/1999 | Deller et al. | 502/170 |
| 5,959,164 | * 9/1999 | Lansink-Rotgerink et al. | 568/896 |

FOREIGN PATENT DOCUMENTS

| | | |
|---|---|---|
| 3406185 | 9/1985 | (DE) . |
| 38 03 895 | 4/1989 | (DE) . |
| 38 03 899 | 4/1989 | (DE) . |
| 39 12 504 | 10/1990 | (DE) . |
| 0519435 | 6/1992 | (DE) . |
| 0 725 037 | 1/1996 | (DE) . |
| 4 427 574 | 2/1996 | (DE) . |

* cited by examiner

COMPACTS BASED ON PYROGENICALLY PRODUCED SILICON DIOXIDE

This application is based on Application No. 196 19 961.1 filed in Germany on May 17, 1997 and Provisional Application Ser. No. 60/021,808 filed in the United States on Jul. 16, 1996, the contents of which are incorporated herewith by reference.

BACKGROUND OF THE INVENTION

1. Field of the Invention

The invention relates to compacts based on pyrogenically produced silicon dioxide, a method of producing them and use thereof as catalyst carriers or catalysts.

2. The Prior Art

Pyrogenically produced silicon dioxide is characterized by extremely fine division and a consequently high specific surface area, very high purity, spherical shape of particles and absence of pores. As a result of these properties, pyrogenically produced oxides are becoming increasingly important as carriers for catalysts (D. Koth, H. Ferch, Chem. Ing. Techn. 52, 628 (1980).

Since pyrogenically produced oxides are very finely-divided, there is some difficulty in shaping them to form catalyst carriers or catalysts.

DE-A 31 32 674 discloses a method of producing compacts from pyrogenically produced oxides, using silica sol as the binder.

DE-A 34 06 185 discloses a method of producing compacts using glaze frit powder as a binder and glycerol as a mold release agent.

DE-B 21 00 778 discloses use of granulates based on pyrogenically produced silicon dioxide for production of catalyst carriers in the form of vinyl acetate monomers.

DE-A 39 12 504 discloses a method of producing compacts wherein aluminum stearate, magnesium stearate and/or graphite are used as mold release agents and urea and methyl cellulose are used as pore-forming agents.

These known compacts are commercially available as AEROSIL silicon dioxide pellets number 350, by Degussa A. G. They contain about 0.4 wt. % Mg.

It is known from EP-B 0 519 435 to compress $SiO_2$ into carriers, using binders, to anneal the resulting carriers and to wash the annealed carrier particles in acid until no further binder actions are given off.

The known methods have the disadvantage that in some catalytic reactions such as vinyl acetate production from ethylene, acetic acid and oxygen, or hydration of ethylene to ethanol, the compacts obtained do not have the required optimum properties such as high purity, high activity, high selectivity, high yield of product and high stability.

SUMMARY OF THE INVENTION

The invention relates to compacts based on pyrogenically produced silicon dioxide and having the following physical and chemical characteristics:

| | |
|---|---|
| Outer diameter | 0.8–20 mm |
| BET surface area | 30–400 m$^2$/g |
| Pore volume | 0.5–1.3 ml/g |
| Breaking strength | 10 to 250N |
| Composition | >99.8 wt. % $SiO_2$ |
| Other constituents | <0.2 wt. % |
| Abrasion | <5 wt. % |
| Apparent weight | 350–750 g/l. |

The invention also provides a method of producing compacts based on pyrogenically produced silicon dioxide and having the following physical and chemical characteristics:

| | |
|---|---|
| Outer diameter | 0.8–20 mm |
| BET surface area | 30–400 m$^2$/g |
| Pore volume | 0.5–1.3 ml/g |
| Breaking strength | 10 to 250N |
| Composition | >99.8 wt. % $SiO_2$ |
| Other constituents | <0.2 wt. % |
| Abrasion | <5 wt. % |
| Apparent weight | 350–750 g/l | characterized in that pyrogenically produced silicon dioxide is homogenized with methyl cellulose, microwax and/or polyethylene glycol with addition of water, dried at a temperature of 80–150° C. and optionally comminuted to a powder, and the powder is compressed into compacts and heat-treated at a temperature of 400 to 1200° C. for a time of 0.5 to 8 hours.

The method according to the invention can be worked on all mixers or mills which ensure good homogenization, e.g., paddle mixers, fluidized-bed, gyratory or air-flow mixers. Mixers of use for additional compaction of the mixed material are particularly suitable, e.g. ploughshare mixers, pan grinders or ball mills. Homogenization can be followed by thorough drying at 80–150° C., followed optionally by comminution so as to obtain a free-flowing powder. The compacts can be produced in hand presses, eccentric presses, isostatic presses, extruders or rotary presses or on compactors.

Before compression, in a special embodiment of the invention, the mixture can have the following composition:
50–90 wt. % silicon dioxide, preferably 65–85 wt. %
0.1–20 wt. % methyl cellulose, preferably 5–15 wt. %
0.1–15% microwax, preferably 5–10 wt. %
0.1–15% polyethylene glycol, preferably 5–10 wt. %

The compacts can have various shapes, such as cylindrical, spherical or annular, with an outer diameter of 0.8 to 20 mm. The compacts are heat-treated at 400–1200° C. for 30 minutes to 8 hours. The amounts used and the pressures applied can be varied so as to adjust the breaking strength, the total specific surface area and the pore volume within a specific range.

The compacts according to the invention can be used either directly as a catalyst or as a catalyst carrier. In the latter case the compacts after manufacture will be brought into contact with a catalytically active substance and optionally activated by suitable after-treatment.

More particularly, compacts made of pyrogenically produced silicon dioxide can be used as carriers for the catalyst for producing vinyl acetate monomer from ethylene, acetic acid and oxygen and as the catalyst carrier in the olefin hydration process.

The compacts according to the invention have the following advantages:
Compared with the compacts according to document DE-A 39 12 504, the compacts according to the invention contain no inorganic constituents apart from silicon dioxide. The known compacts have the disadvantage of containing about 0.4 wt. % Mg, which is leached out during the olefin hydration process.

The compacts according to the invention, by contrast, have improved hydrothermal stability during hydration processes of this kind. They also have high purity and a large pore volume.

The invention also provides a carrier catalyst for production of vinyl acetate monomer (VAM) containing catalytically active components in the form of palladium, gold and alkali-metal compounds on the silicon dioxide carrier according to the invention, and a method of production and use thereof.

Carrier catalysts containing gold, palladium and alkali-metal compounds are used for production of vinyl acetate. To this end, ethane, acetic acid and molecular oxygen or air in the gas phase are reacted, optionally with addition of inert gases, at temperatures between 100 and 250° C. and normal or elevated pressure in the presence of the carrier catalyst. A method of production of this kind is known from documents DE 16 68 088, U.S. Pat. No. 4,048,096 and EP 0 519 435 B1.

These patent specifications also disclose a method of producing carrier catalysts containing gold, palladium and alkali-metal compounds. Depending on the embodiment, catalysts are obtained with a homogeneous distribution of noble metal across the carrier cross-section and with a relatively marked shell profile.

These catalysts are usually obtained by impregnating the carriers with a basic solution and a solution containing gold or palladium salts, the impregnation steps occurring simultaneously or successively, with or without intermediate drying. The carrier is then washed in order to remove any chloride components. Before or after washing, the insoluble noble-metal compounds precipitated on the carrier are reduced. The resulting catalyst precursor is dried and, in order to active the catalyst, is impregnated with alkali-metal acetates or alkali-metal compounds which under the reaction conditions are converted partly or completely into alkali-metal acetates in the production of vinyl acetate monomer.

The catalyst can be reduced in the aqueous phase or in the gas phase. Formaldehyde or hydrazine are suitable for reduction in the aqueous phase. Reduction in the gas phase can be brought about with hydrogen or forming gas (95 vol. % $N_2$+5 vol. % $H_2$) or ethane. According to EP 0 634 209 the reduction is brought about with hydrogen at temperatures between 40 and 260° C., preferably between 70 and 200° C. Frequently, however, the catalyst is first activated with alkali-metal acetate before being directly reduced with ethane in the production reactor.

In the production process the catalyst is first slowly loaded with the reactants. During this starting phase the activity of the catalyst increases, usually taking some days or weeks to reach its final level.

The object of the present invention is to disclose a carrier catalyst for production of vinyl acetate monomer and having the same or improved selectivity and higher activity than known catalysts.

The invention provides a carrier catalyst containing catalytically active components in the form of palladium, gold and alkali-metal acetate on the silicon dioxide carrier according to the invention.

The carrier material for the catalyst can be the compact according to the invention based on pyrogenically produced silicon dioxide. An important feature is that the catalyst carriers retain their mechanical strength under the reaction conditions of the catalytic process, more particularly under the influence of acetic acid.

The compacts according to the invention can be formed into the form of pellets, cylinders, tablets or other conventional shapes for fixed-bed catalysts.

The compacts according to the invention are impregnated with a solution containing palladium and gold. Together with the solution containing noble metal or in any sequence, the compacts according to the invention are impregnated with a basic solution which can contain one or more basic compounds. The basic compound or compounds are for converting the palladium and gold into their hydroxides.

The compounds in the basic solution can comprise alkali-metal hydroxides, alkali-metal bicarbonates, alkali-metal carbonates, alkali-metal silicates or mixtures of these substances. Preferably potassium hydroxide and sodium hydroxide are used.

The solution containing noble metals can be produced by using palladium salts, e.g. palladium chloride, sodium or potassium palladium chloride or palladium nitrate. The gold salts can be gold (III) chloride or tetrachloro-auric palladium chloride or sodium palladium chloride and tetrachloro-auric acid.

Impregnation of the compacts according to the invention with the basic solution influences deposition of noble metals into the compact. The basic solution can be brought into contact with the compact according to the invention either at the same time as the noble-metal solution or in any sequence therewith. When the compact according to the invention is impregnated successively with the two solutions, the first impregnation step can be followed by intermediate drying.

Preferably the compact according to the invention is first impregnated with the basic compound. Subsequent impregnation with the solution containing palladium and gold results in precipitation of palladium and gold in a surface shell on the compact according to the invention. The reverse sequence of impregnations usually results in a relatively homogeneous distribution of the noble metals over the cross-section of the compact according to the invention. If the process is suitably guided, however, even with the reverse impregnation sequence, catalysts with a defined shell can be obtained (see e.g., U.S. Pat. No. 4,048,096). Catalysts with a homogeneous or nearly homogeneous noble-metal distribution usually have lower activity and selectivity.

Catalysts with shell thickness below 1 mm, preferably below about 0.5 mm, are particularly suitable. The shell thickness is influenced by the quantity of the basic compound applied to the carrier material, relative to the desired quantity of noble metals. The higher this proportion, the smaller is the thickness of the shell formed. The proportion of basic compound to noble-metal compounds required for a desired shell thickness depends on the nature of the carrier material and on the chosen basic compound and the noble-metal compounds. The required proportion is advantageously obtained by a few preliminary tests. The resulting shell thickness can be determined in simple manner by cutting open the catalyst particles.

The minimum required amount of the basic solution can be found from the stoichiometrically calculated quantity of hydroxide ions needed for converting the palladium and gold into the hydroxides. As a guiding value, the basic compound for a shell thickness of 0.5 mm should be used in a 1 to 10-fold stoichiometric excess.

The compacts according to the invention are coated with the basic compounds and the noble-metal salts by the method of pore volume impregnation. If the method includes intermediate drying, the volumes of the two solutions are chosen so as to make up about 90 to 100% of the absorption capacity of the compacts according to the invention. If there is no intermediate drying, the sum of the individual volumes of the two impregnating solutions must conform to the above condition, the proportions of the individual volumes varying from 1:9 to 9:1. A volume ratio of 3:7 to 7:3, preferably 1:1, is preferred. In both cases the preferred solvent is water. However, other suitable organic or aqueous organic solvents can be used.

The reaction between the noble-metal salt solution and the basic solution to form insoluble noble-metal compounds occurs slowly and, depending on the method of preparation, usually takes from 1 to 24 hours. The water-insoluble noble-metal compounds are then treated with reducing agents. The reduction can be wet, e.g. with aqueous hydrazine hydrate, or in the gas phase with hydrogen, ethane, forming gas or methanol vapors. Reduction can occur at normal temperature or elevated temperature and at normal pressure or elevated pressure, optionally with addition of inert gases.

Before or after reduction of the noble-metal compounds, any chloride on the carrier is removed by thorough washing. After washing the catalyst should contain less than 500 or preferably less than 200 ppm of chloride.

The catalyst precursor obtained after reduction is dried and then impregnated with alkali-metal acetates or alkali-metal compounds which, under the reaction conditions, are converted partly or completely into alkali-metal acetates during production of vinyl acetate monomer. Preferably potassium acetate is used for impregnation, i.e., the required amount of potassium acetate is dissolved in a solvent, preferably water, having a volume approximately equal to the capacity of the starting amount of carrier material to absorb the chosen solvent. This volume is approximately equal to the total pore volume of the carrier material.

The finished catalyst is then dried to a residual moisture content of less than 2%. Drying can be brought about in air, or optionally under nitrogen inert gas.

For synthesis of vinyl acetate monomer it is advantageous to coat the catalyst with 0.2 to 4, preferably 0.3 to 3% palladium, 0.1 to 2, preferably 0.15 to 1.5 wt. % gold, and 1 to 10, preferably 3.5 to 10 wt. % potassium acetate, in each relative to the weight of carrier used. In the case of catalyst carriers with an apparent density of 500 g/l, these concentrations correspond to concentrations by volume of 1.0 to 20 g/l palladium, 0.5 to 10 g/l gold and 5 to 50 g/l potassium acetate. The impregnation solutions are prepared by dissolving the corresponding quantities of palladium and gold compounds in a volume of water corresponding to about 90 to 100% of the water absorption capacity of the starting amount of carrier material. The basic solution is prepared in similar manner.

The invention also relates to hydration of olefins to the corresponding alcohols in the presence of phosphoric acid or another active component, e.g., a heteropoly acid, as a catalyst carrier on the compact according to the invention.

One such method is described e.g. in EP 0 578 441 A2. In this method, water and ethylene are reacted at temperatures between 225 and 280° C. and pressures between 20 and 240 bar to form ethanol. A water/ethylene molar ratio in the range from 0.15 to 0.5 is used. The catalyst load, measured in grams of water/ethylene mixture per minute and per milliliter catalyst, can be chosen in the range from 0.01 to 0.1 g/(min×ml). The by-product of this reaction is diethyl ether.

Isopropanol is prepared by hydration of propylene under similar conditions but at a reduced temperature in the range between 180 and 225° C. The by-product of this reaction is n-propanol.

The catalyst carriers for the phosphoric-acid active component, according to EP 0 578 441 A2, can be pellets of synthetic silicon dioxide with high breaking strength, high porosity and few metallic impurities. The pores of the carrier are for holding the active component. The average pore radius for the hydration process is in the range between 1 and 50 nm.

During operation, catalysts are subject to aging, shown by a reduction in activity and/or selectivity. Deactivation is frequently due to reduction of the specific surface area of the carrier caused by high temperature.

The specific surface area of the carrier is closely related to its pore structure. In addition, high-surface solids usually have a completely or mainly amorphous structure which tends to change to a thermodynamically stable state, with growth of crystallites and reduction of the specific surface.

It has been shown that catalyst carriers containing silicon dioxide are also subject to such aging. Hydration conditions accelerate aging. It is also known that impurities, particularly alkali metals, also promote the aging of carriers containing silicon dioxide under hydrothermal conditions (see e.g. R. K. Iler in "The Chemistry of Silica", page 544, John Wiley & Sons (1979)).

The catalyst carriers described in EP 0 393 356 and based on pyrogenically produced silicon dioxide are also subject, under hydrothermal conditions, to aging, when small pores grow into larger pores and lose specific surface area. The pore volume does not initially vary appreciably.

The object of the present invention therefore is to disclose silicon dioxide-containing catalyst carriers which have better resistance to aging when used under hydrothermal conditions.

This object is achieved by use of catalysts containing an active component on a compact according to the invention.

The use according to the invention is particularly advantageous for hydration of olefins. However, stabilization of the carrier is also advantageous in other catalytic reactions under hydrothermal conditions.

In the case of hydration of olefins, the active component incorporated in the catalyst carrier is phosphoric acid. To this end, the carrier is immersed in an aqueous solution of phosphoric acid and impregnated therewith. Use can be made of phosphoric acid solutions containing 15 to 85 wt. % phosphoric acid relative to the total weight of the solution.

One main application of hydration of olefins is to hydration of ethylene for producing ethanol and diethyl ether or hydration of propylene for producing isopropanol. The reaction conditions known from the prior art are applied.

The following is an investigation of the change in the pore structure of catalyst carriers containing silicon dioxide under hydrothermal conditions. A known carrier is compared with a carrier according to the invention.

Figure 1:
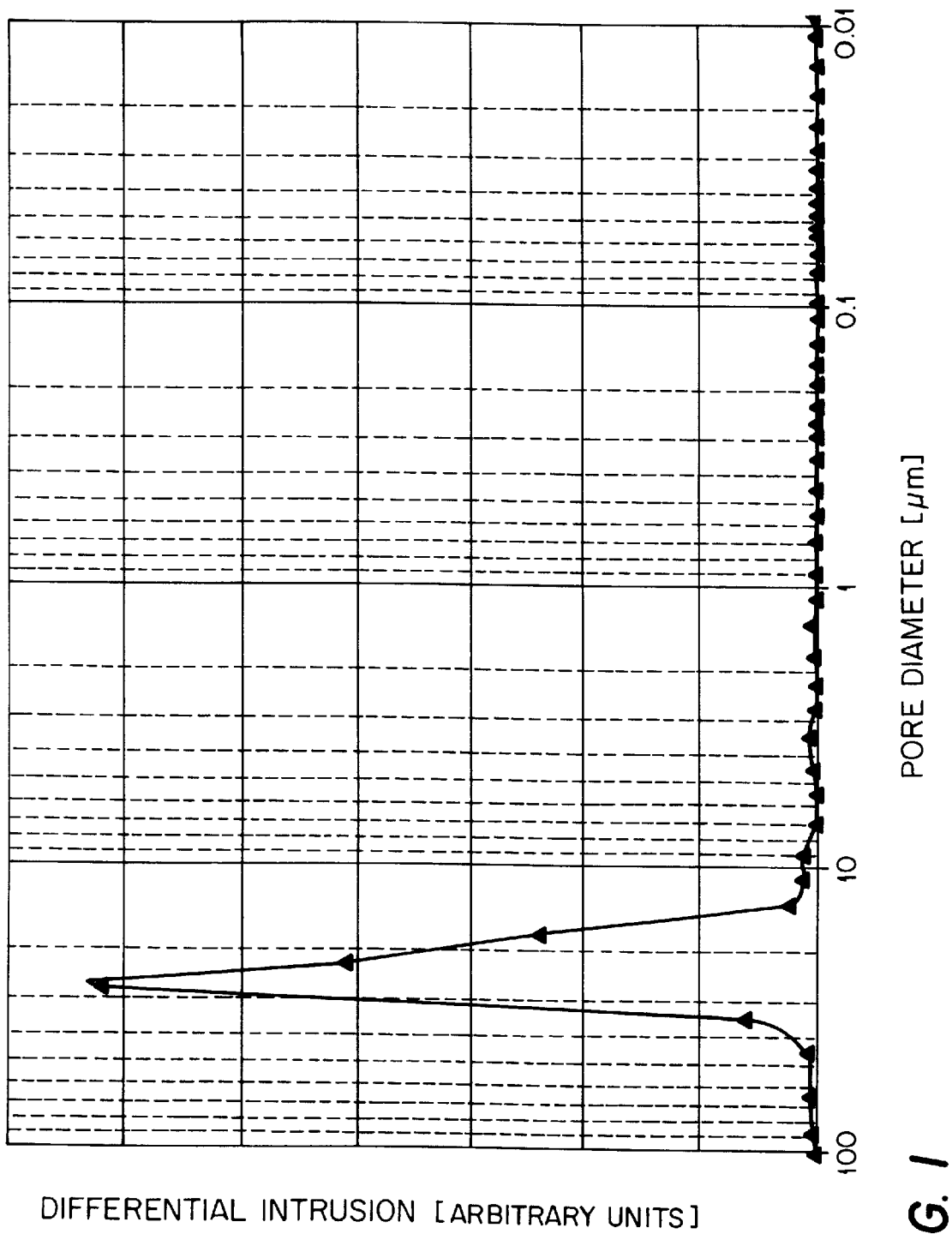
FIG. 1 shows the pore construction of a catalyst carrier containing Mg after a hydrothermal aging test and FIG. 2 shows the pore structure of a catalyst carrier according to the invention after a hydrothermal aging test.
Figure 2:
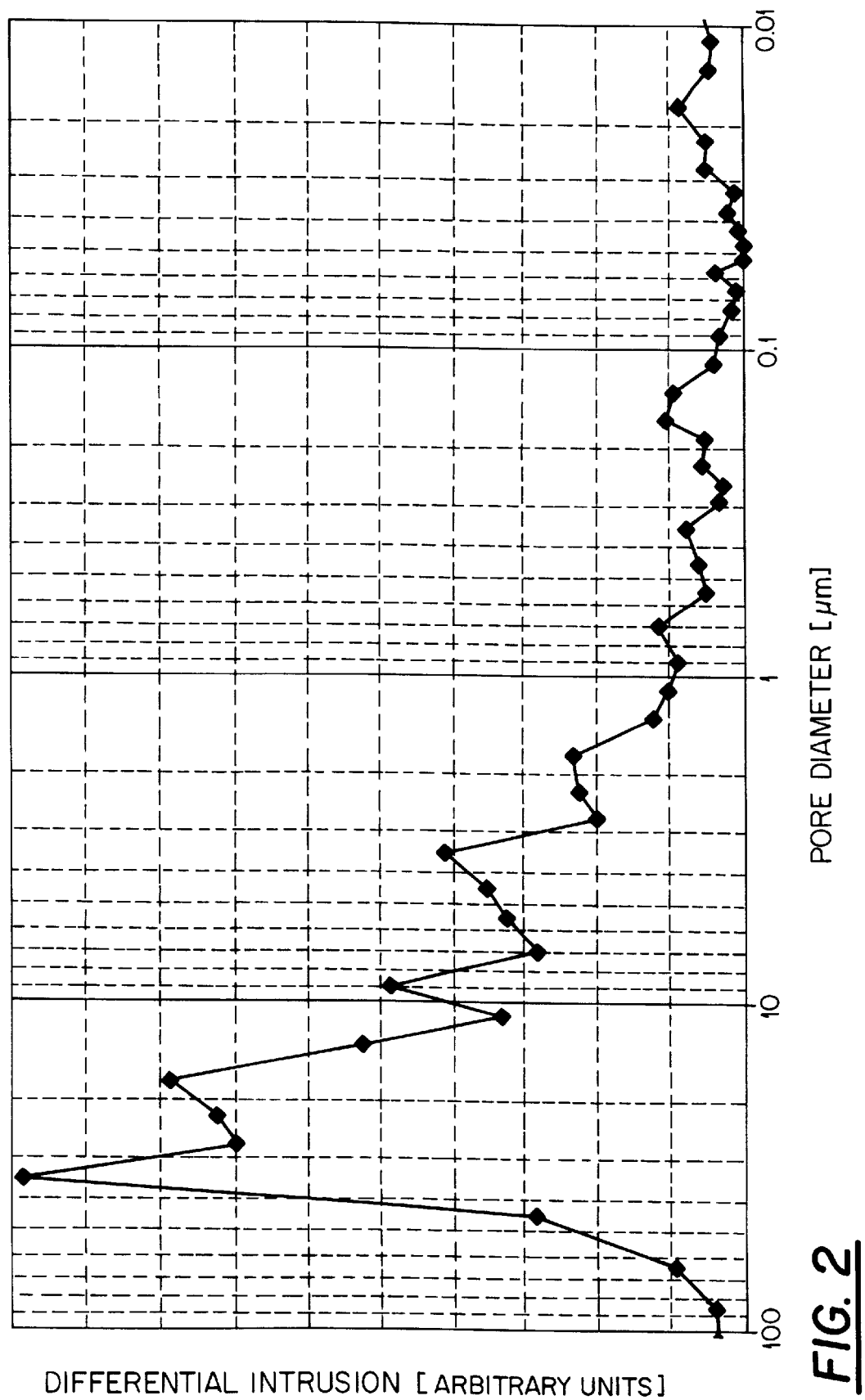

The pore distribution curves shown in FIGS. 1 and 2 were obtained by known Hg porosimetry. They show the differential penetration (intrusion) of mercury in dependence on pore diameter. Arbitrary units were chosen for differential intrusion and in each case the curves were extended over the available region of the graph.

The pyrogenically produced silicon dioxide can have the following physical and chemical characteristics:

|  | AEROSIL OX 50 | AEROSIL 90 | 130 | 150 | 200 | 300 | 380 |
|---|---|---|---|---|---|---|---|
| BET surface area m²/g | 50 ± 15 | 90 ± 15 | 130 ± 25 | 150 ± 15 | 200 ± 25 | 300 ± 30 | 380 ± 30 |
| Average size of primary particles, nm | 40 | 20 | 16 | 14 | 12 | 7 | 7 |
| Tamping density[1], g/l | about 130 | about 80 | about 50 | about 50 | about 50 | about 50 | about 50 |
| Loss on drying[2] (2 hours at 105° C.), % | <1.5 | <1 | <1.5 | <0.5[7] | <1.5 | <1.5 | <1.5 |
| Loss on annealing[2)5] 2 hours at 1000° C.) % | <1 | <1 | <1 | <1 | <1 | <2 | <2.5 |
| pH[3] (in 4% aqueous dispersion) | 3.8–4.8 | 3.6–4.5 | 3.6–4.3 | 3.6–4.3 | 3.6–4.3 | 3.6–4.3 | 3.6–4.3 |
| $SiO_2$[6], | >99.8 | >99.8 | >99.8 | >99.8 | >99.8 | >99.8 | >99.8 |
| $Al_2O_3$[6], | <0.08 | <0.05 | <0.05 | <0.05 | <0.05 | <0.05 | <0.05 |
| $Fe_2O_3$[6], | <0.01 | <0.003 | <0.003 | <0.003 | <0.003 | <0.003 | <0.003 |
| $TiO_2$[6], | <0.03 | <0.03 | <0.03 | <0.03 | <0.03 | <0.03 | <0.03 |
| HCl[6)8], | <0.025 | <0.025 | <0.025 | <0.025 | <0.025 | <0.025 | <0.025 |
| Retained on sieve[4] (after Mocker, 45 μm) % | <0.2 | <0.05 | <0.05 | <0.05 | <0.05 | <0.05 | <0.05 |

[1] According to DIN 53 194
[2] According to DIN 55 921
[3] According to DIN 53 200
[4] According to DIN 53 580
[5] Relative to substance dried at 105° C. for 2 hours
[6] Relative to substance annealed at 1000° for 2 hours
[8] The HCl content is a component of the loss on annealing AEROSIL is produced by spraying a volatile silicon compound into a hydrogen and air detonating gas flame. In most cases, silicon tetrachloride is used. This substance, under the influence of the water produced in the detonating-gas reaction, is hydrolyzed to silicon dioxide and hydrochloric acid. After leaving the flame, the silicon dioxide enters a "coagulation zone" in which the AEROSIL primary particles and primary aggregates form agglomerates. The aerosol-like product formed at this stage is separated from the accompanying gaseous substances in cyclones and then after-treated with moist hot air. By this method, the residual hydrochloric acid content can be reduced below 0.025%. Since the AEROSIL at the end of this process has an apparent density of only about 15 g/l, the process also includes compaction in vacuo, which can give tamping densities of about 50 a/l.

The particle sizes of the thus-obtained products can be varied by means of the reaction conditions, such as the flame temperature, the proportion of hydrogen or oxygen, the amount of silicon tetrachloride, the residence time in the flame or the length of the coagulation section.

The BET surface area is determined to DIN 66 131, using nitrogen. The pore volume is calculated from the sum of the micro, meso and macropore volumes. The breaking strength is determined by using the breaking-strength tester produced by Messrs. Erwaka, Type TBH 28.

The micro and meso pores are determined by recording an $N_2$ isotherm and evaluating it after BET, de Boer and Barret, Joyner, Halenda.

The macropores are determined by the Hg pressing-in method.

The abrasion is determined by means of the abrasion and friability tester produced by Messrs. Erwaka, Type TAR.

DETAILED DESCRIPTION OF PREFERRED EMBODIMENTS OF THE INVENTION

EXAMPLES 1–5

71.5 wt. % AEROSIL 200 silicon dioxide
13 wt. % methyl cellulose
7 wt. % microwax and
8.5 wt. % polyethylene glycol were compacted with adhesion of water, dried at 110° C. for 16 hours, comminuted to obtain a free-flowing powder and shaped into compacts in an eccentric press. The crude pellets were calcined at 750° C. for 6 hours.

The resulting compacts had the following physical and chemical characteristics:

| Example | 1 | 2 | 3 | 4 | 5 |
|---|---|---|---|---|---|
| Shape of pellet | Cylinders | Cylinders | Cylinders | Cylinders | Rings |
| Outer diameter × height × inner diameter (mm) | 3 × 3 | 4 × 4 | 5 × 5 | 5 × 5 | 9 × 5 × 3 |
| BET surface area (m²/g) | 170 | 164 | 168 | 163 | 165 |
| Pore volume (ml/g) | 0.75 | 0.84 | 0.84 | 0.97 | 0.79 |
| Breaking strength (N) | 49 | 42 | 60 | 31 | 22 |
| Abrasion (wt. %) | 0.9 | 1.6 | 1.3 | 3.8 | 3.8 |
| Apparent weight (g/l) | 535 | 485 | 470 | 430 | 400 |
| $SiO_2$ content wt. % | 99.9 | 99.9 | 99.9 | 99.9 | 99.9 |

EXAMPLE 6

75 wt. % AEROSIL 200 silicon dioxide
11.5 wt. % methyl cellulose
6 wt. % microwax and
7.5 wt. % polyethylene glycol were compacted with addition of water, dried at 110° C. for 16 hours, comminuted to obtain a free-flowing powder and shaped into compacts in an eccentric press. The crude pallets were heat-treated at 750° C. for 6 hours.

The resulting compacts had the following physical and chemical characteristics:

| | |
|---|---|
| Shape of pellets | Cylinders |
| Outer diameter × height (mm) | 5 × 5 |
| BET surface area (m$^2$/g) | 168 |
| Pore volume (ml/g) | 0.71 |
| Breaking strength (N) | 61 |
| Abrasion (wt. %) | 2.3 |
| Apparent weight (g/l) | 510 |
| SiO$_2$ content (wt. %) | 99.9 |

EXAMPLES 7 and 8

71.5 wt. % of AEROSIL 300/AEROSIL 130 silicon dioxide (EXAMPLE 7) (EXAMPLE 8)

13 wt. % methyl cellulose 7 wt. % microwax and 8.5 wt. % polyethylene glycol were compacted with addition of water, dried at 110° C. for 16 hours, comminuted into a free-flowing powder and shaped into compacts in an eccentric press. The crude pellets were calcined at 750° C. for 6 hours.

The resulting compacts had the following physical and chemical characteristics:

| Example | 7 | 8 |
|---|---|---|
| Outer diameter × height (mm) | 5 × 5 | 5 × 5 |
| BET surface area (m$^2$/g) | 210 | 117 |
| Pore volume (ml/g) | 0.85 | 0.89 |
| Breaking strength (N) | 55 | 39 |
| Abrasion (wt. %) | 2.0 | 2.4 |
| Apparent weight (g/l) | 465 | 450 |
| SiO$_2$ content (wt. %) | 99.9 | 99.9 |

COMPARATIVE EXAMPLE 1

A compact not according to the invention (catalyst carrier 350, Messrs. Degussa, with 0.4 wt. % Mg (elementary), BET surface area 180 m$^2$/g, apparent density 490 g/l, total pore volume 0.8 cm$^3$/g, pellets 6 mm in diameter and 5.5 mm high) was loaded with phosphoric acid (60 wt. %) and left for 41 hours in a high-pressure installation at a water-vapor pressure of 15 bar and at 350° C. The pore distribution of the aged catalyst was determined by Hg porosimetry. The measured pore distribution is shown graphically in FIG. 1.

The hydrothermally aged carriers had a maximum pore distribution at pore diameters between 20 and 30 μm. The proportion of pores smaller than 10 μm in diameter was practically zero.

EXAMPLE 9

A carrier according to the invention as in Example 3 (mg content <50 micrograms/g) was loaded with phosphoric acid (60 wt. %) and left for 40 hours in a high-pressure installation at a water-vapor pressure of 15 bar and at 350° C. The pore distribution of the aged catalyst was determined by Hg porosimetry as before. The pore distribution is shown graphically in FIG. 2.

The maximum pore distribution occurs at 30 μm. Compared with the catalyst used in comparative example 1, the catalyst according to the invention (carrier or catalyst), even after aging, had a greater proportion of small pores less than 10 μm in diameter.

COMPARATIVE EXAMPLE 2

A catalyst support prepared from pyrogenic silica (BET surface area 180 m$^2$/g, apparent density 490 g/l, total pore volume 0.8 cm$^3$/g, tablets 6 mm in diameter and 5.5 mm high, with 0.4 wt. % (elemental) Mg, was contacted with 10% hydrochloric acid at room temperature for 14 hours in accordance with Example 1 of EP 0 519 435 and was then washed free of chloride under running water, and dried.

A palladium-gold-potassium acetate catalyst was then prepared on the pre-treated catalyst support.

The concentration of the impregnating solutions was selected such that the finished catalyst contained a concentration of 0.55 wt. % palladium, 0.25 wt. % gold and 5.0 wt. % potassium acetate.

In a first step, the support was impregnated initially with a basic solution comprising sodium hydroxide in water. The volume of the aqueous NaOH solution corresponded to 50% of the water absorption of the dry support. After impregnation with sodium hydroxide, the support was impregnated immediately, without interim drying, with an aqueous noble metal solution prepared from sodium palladium chloride and tetrachloroauric acid, the volume of the latter solution also corresponding to 50% of the water absorption capacity of the dry support material.

After waiting for 1.5 hours for the noble metal compounds to hydrolyse, the support particles were washed free of chloride. The catalyst was dried and was reduced with forming gas at 450° C. in the gas phase. The catalyst was then impregnated with an aqueous potassium acetate solution and was once more dried. Drying was in the gas phase with nitrogen.

The sodium hydroxide concentration of the basic solution was calculated such that there formed on the support particles a noble metal-containing <1.0 mm shell.

EXAMPLE 10

A palladium-gold-potassium acetate catalyst as described in Comparative Example 2 was prepared on the catalyst support according to the invention in accordance with Example 3 (Mg content <50 micrograms/g), but 6.0 mm in diameter and 5.5 mm high. By contrast with Comparative Example 2, however, no pretreatment with 10% hydrochloric acid was carried out.

EXAMPLE 11

A palladium-gold-potassium acetate catalyst was prepared in accordance with Example 10 on the catalyst support according to the invention in accordance with Example 5, but having the dimensions 8×5×3 mm and having beveled edges.

WORKING EXAMPLE 1

The activity and selectivity of the catalysts form Comparative Example 2 and Examples 10 and 11 were measured during a test of up to 24 hours duration.

The catalysts were tested in an oil-heated tubular-flow reactor (reactor length 710 mm, internal diameter 23.7 mm) at standard pressure and at a space velocity (GHSV) of 550/h$^{-1}$, using the following gas composition: 75 vol. % ethane, 16.6 vol. % acetic acid, 8.3 vol. % oxygen. The catalysts were examined within the temperature range 120 to 165° C. as measured in the catalyst bed.

The reaction products were analyzed by on-line gas chromatography at the reactor discharge. The measure of catalyst activity adopted was the catalyst space-time yield in grams of vinyl acetate monomer per hour and kilograms of catalyst (g VAM/(h×kg$_{Cat}$).

Carbon dioxide which is formed in particular by ethane combustion was also determined and was used in evaluating catalyst selectivity.

Table 1 shows the results of examining the catalysts from Comparative Example 2 and Examples 10 and 11. The activity and selectivity of the catalyst in accordance with Comparative Example 2 were in each case expressed as 100%.

TABLE 1

| Catalyst | Activity [g VAM/(h × kg$_{Cat}$)] as [%] of Comp. Ex. 2 | Selectivity CO$_2$ in exhaust gas in [surface area %], as [%] of Comp. Ex. 2 | Catalyst temperature [° C.] |
|---|---|---|---|
| Comp. Ex. 2 | 100 | 100 | 159.6 |
| Example 10 | 121.1 | 72.0 | 155.6 |
|  | 122.7 | 96.8 | 161.1 |
| Example 11 | 106.8 | 58.5 | 142.1 |
|  | 124.9 | 103.9 | 154.1 |

The results show that the catalysts according to the invention have a markedly high. activity than the Comparative catalyst, with a comparable or even improved selectivity.

What is claimed is:

1. A compact composition comprising a pyrogenically produced silicon dioxide having the following physical and chemical characteristics:

| | |
|---|---|
| Outer diameter | 0.8–20 mm |
| BET surface area | 30–400 m$^2$/g |
| Pore volume | 0.5–1.3 ml/g |
| Breaking strength | 10–250N |
| Composition | >99.8 wt. % SiO$_2$ |
| Other constituents | <0.2 wt. % |
| Abrasion | <5 wt. % |
| Apparent weight | 350–750 g/l. |

2. A catalyst or catalyst carrier comprising the compact composition according to claim 1.

3. A catalyst composition for production of vinyl acetate monomer comprising palladium, gold and alkali-metal acetate supported on a compact composition according to claim 1.

4. A catalyst composition according to claim 3 comprising 0.2 to 4 wt. % palladium, 0.1 to 2 wt. % gold and 1 to 10 wt. % alkali metal acetate based on total weight of compact composition.

5. A method of producing the catalyst composition according to claim 3 comprising (1) impregnating the compact composition with a basic solution and a solution containing gold and palladium salts, the impregnating occurring simultaneously or successively with or without intermediate drying, (2) washing the impregnated compact composition to remove any chloride components and reducing insoluble components present in the compact composition before or after washing to form a catalyst precursor, (3) drying resulting catalyst precursor and (4) impregnating the catalyst precursor after drying with alkali-metal acetates or alkali-metal compounds which under reaction conditions for production of vinyl acetate monomer are converted partly or completely into alkali-metal acetates during production of vinyl acetate monomer.

6. A compact composition according to claim 1 in which the SiO$_2$ content is ≧99.9 wt %.

7. A method of producing a compact composition based on a pyrogenically produced silicon dioxide having the physical and chemical characteristics according to claim 1 which comprises (1) mixing the pyrogenically produced silicon dioxide with methyl cellulose, microwax, polyethylene glycol and an aqueous medium to form a homogenized mixture, (2) drying the homogenized mixture obtained in (1) at a temperature of 80–150° C. and, optionally (3) comminuting dried homogenized mixture obtained in (2) to form a free-flowing powder, (4) compressing the free-flowing powder into compacts of a desired shape, and (5) heat-treating shaped compacts at a temperature of 400 to 1200° C. for 0.5 to 8 hours.

* * * * *